United States Patent [19]

Cue, Jr. et al.

[11] Patent Number: 4,620,019
[45] Date of Patent: Oct. 28, 1986

[54] S-6-FLUORO-4-AMINOCHROMAN-4-CARBOXYLIC ACID DERIVATIVES USEFUL AS INTERMEDIATES FOR SORBINIL

[75] Inventors: Berkeley W. Cue, Jr., Gales Ferry; Bernard S. Moore, Waterford, both of Conn.

[73] Assignee: Pfizer Inc., New York, N.Y.

[21] Appl. No.: 643,895

[22] Filed: Aug. 23, 1984

[51] Int. Cl.⁴ .......................................... C07D 311/68
[52] U.S. Cl. .................................... 549/404; 548/309
[58] Field of Search ......................................... 549/404

[56] References Cited

U.S. PATENT DOCUMENTS

| | | | |
|---|---|---|---|
| 4,117,230 | 9/1978 | Sarges | 548/309 |
| 4,130,714 | 12/1978 | Sarges | 548/309 |
| 4,286,098 | 8/1981 | Sarges | 548/309 |
| 4,348,526 | 9/1982 | Sarges | 548/309 |
| 4,431,828 | 2/1984 | Cue, Jr. et al. | 549/401 |
| 4,435,578 | 3/1984 | Cue et al. | 548/309 |

OTHER PUBLICATIONS

Sarges et al., J. Org. Chem., 47, 4081, (1982).

Primary Examiner—Nicky Chan
Attorney, Agent, or Firm—Charles J. Knuth; Albert E. Frost; Robert K. Blackwood

[57] ABSTRACT

Chiral sorbinil intermediates of the formula

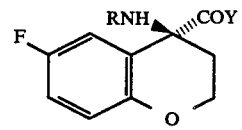

wherein R is hydrogen or benzyloxycarbonyl and Y is hydroxy or amino, processes therefor, and processes for the conversion thereof to sorbinil.

6 Claims, No Drawings

S-6-FLUORO-4-AMINOCHROMAN-4-CARBOXYLIC ACID DERIVATIVES USEFUL AS INTERMEDIATES FOR SORBINIL

BACKGROUND OF THE INVENTION

S-6-Fluorospiro[chroman-4,4'-imidazolidine]-2',5'-dione, also named S-2,3-dihydro-6-fluorospiro[4H-1-benzopyran-4,4'-imidazolidine]-2',5'-dione (U.S.A.N.: sorbinil) of the formula

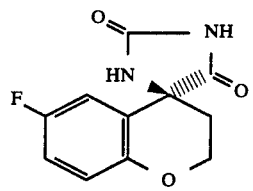

is a highly potent aldose reductase inhibitor having especial value in effectively controlling the chronic complications of diabetes mellitus. (Sarges, U.S. Pat. No. 4,130,714.)

The present invention is directed to chiral compounds of the formula

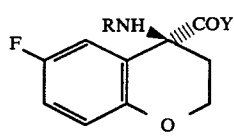

wherein R is hydrogen or benzyloxycarbonyl and Y is hydroxy or amino, which are useful as intermediates in the synthesis of sorbinil; processes useful in the preparation of these intermediates; and processes for the conversion of these intermediates to sorbinil.

Heretofore, sorbinil was prepared by resolution of the corresponding racemic 6-fluorospiro[chroman-4,4'-imidazolidine]-2',5'-dione, of the formula

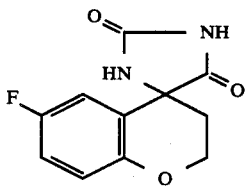

with highly toxic brucine as the resolving agent in high volumes of solvent (Sarges, U.S. Pat. No. 4,130,714), or with (−)-3-aminomethylpinane, or (+)-3-aminomethylpinane or (−)-2-amino-2-norpinane/quinine combinations (Sysko, European Patent Application publication No. 109,231). Sorbinil has also been prepared by an alternative synthesis in which the required chirality is induced during the synthetic sequence (Sarges, U.S. Pat. No. 4,286,098).

Our recent U.S. Pat. No. 4,435,578 describes an improved process for sorbinil in which the ureido compound of the formula

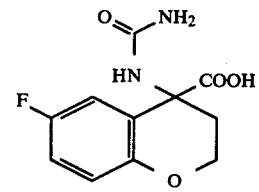

is resolved to form S-6-fluoro-4-ureidochroman-4-carboxylic acid as either its D-(+)-(1-phenethyl)amine or its L-(−)-ephedrine salt, followed by simple cyclization to sorbinil in glacial acetic acid.

Surprisingly, we have now also found that precursor 6-fluoro-4-(benzyloxycarbonylamino)-4-carboxylic acid, of the formula

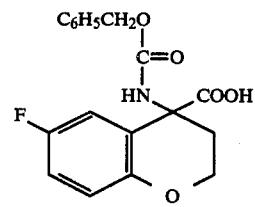

is readily resolved as its 1-(−)-alpha-methylbenzylamine salt to produce S-6-fluoro-4-(benzyloxycarbonylamino)chroman-4-carboxylic acid [of the formula (II) wherein R is benzyloxycarbonyl and Y is hydroxy]. The latter can be converted to other heretofor unavailable intermediates of the formula (II) which in turn are directly convertible to sorbinil, thus providing improved synthetic methods for this valuable medicinal agent. The racemic precursor is conveniently derived from the above racemic imidazolidine of the formula (A) via the amino acid of the formula

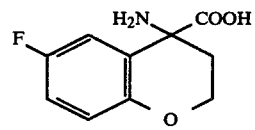

In this manner, outstanding yields of sorbinil are obtained with a readily available, relatively inexpensive optically active amine. At the same time the use of a highly toxic resolving agent is avoided. The efficiency of this process is further enhanced by isolating the undesired enantiomer from mother liquors and recycling to fresh racemate, via precursor 6-fluoro-4-chromanone.

SUMMARY OF THE INVENTION

The present invention encompasses chiral compounds of the above formula (II), including cationic salts when Y is hydroxy and acid addition salts when R is hydrogen, thus defining:

S-6-fluoro-4-(benzyloxycarbonylamino)chroman-4-carboxylic acid and its cationic salts;

S-6-fluoro-4-aminochroman-4-carboxylic acid, its cationic salts, and its acid addition salts;

S-6-fluoro-4-(benzyloxycarbonylamino)chroman-4-carboxamide; and

S-6-fluoro-4-aminochroman-4-carboxamide and its acid addition salts.

Said cationic salts include, but are not limited to those with the alkali metals (e.g., sodium, potassium), alkaline earths (e.g., calcium, magnesium) and amines (e.g., ammonia, methylamine, benzylamine, 1-(−)-alpha-methylbenzylamine, triethylamine); and quaternary ammonium salts. Said acid addition salts include, but are not limited to, those with hydrochloric acid, nitric acid, sulfuric acid, benzenesulfonic acid, tartaric acid, and the like.

Key to the present invention is the discovery of crystalline 1-(−)-alpha-methylbenzylamine salt of S-4-(benzyloxycarbonylamino)-6-fluorochroman-4-carboxylic acid and the process of optical resolution therefor, which is also part of the present invention. This key salt is readily converted to the free acid form of the compound (II) wherein R is benzyloxycarbonyl and Y is hydrogen, and thence to one or another of the previously unavailable chiral compounds of the formula (II) each of which is convertible by a one-step method to sorbinil.

The present invention also encompasses one step processes for sorbinil as follows:

(a) A process for sorbinil which comprises treatment of S-6-fluoro-4-(benzyloxycarbonylamino)chroman-4-carboxamide with substantially one equivalent of a strong base in an anhydrous, reaction-inert, organic solvent, particularly as carried out at 50°–100° C. wherein the solvent is a ($C_1$–$C_5$)alkanol and the base is an alkali ($C_1$–$C_5$)alkoxide. Most preferred are methanol and sodium methoxide.

(b) A process for sorbinil which comprises the reaction of S-6-fluoro-4-aminochroman-4-carboxamide with at least one equivalent of a compound of the formula

wherein both X and Y are 1-imidazolyl or X and Y are each independently chloro, trichloromethoxy, ($C_1$–$C_5$)-alkoxy, phenoxy or benzyloxy, in the presence of substantially one equivalent of a strong base when one or both of X and Y are other than chloro and sufficient base to neutralize any HCl coproduced when either X or Y or both are chloro, in an anhydrous, reaction-inert, organic solvent. The reaction is preferably carried out at 50°–100° C. with both X and Y as ($C_1$–$C_5$) alkoxy, the solvent as a ($C_1$–$C_5$)alkanol and the base as an alkali metal ($C_1$–$C_5$)alkoxide. Most preferred is with both X and Y as methoxy in methanol with sodium methoxide as base.

(c) A process for sorbinil which comprises treating S-6-fluoro-4-aminochroman-4-carboxylic acid with at least one molar equivalent of an alkali metal cyanate in a reaction-inert solvent in the presence of at least one molar equivalent of an acid, preferably at 20°–100° C. with both the solvent and the acid as acetic acid.

DETAILED DESCRIPTION OF THE INVENTION

The transformations and intermediates of the present invention are shown schematically in Scheme I. These transformations are readily carried out.

Key to preparation of the present chiral intermediates (IIa-d) is the resolution of racemic 6-fluoro-6-(benzyloxycarbonylamino)chroman-4-carboxylic acid (III). In this process, the racemic compound is combined with 1-(−)-alpha-methylbenzylamine in a suitable solvent. Usually about mole for mole of acid and amine are employed, although the amount of amine can be varied from as little as 0.5 mole/mole to a large excess. To avoid precipitation of racemic free acid, it is preferred to employ at least about mole/mole. The solvent is usually organic in nature. The preferred solvent system is a combination of a lower alkanol (of 1 to 5 carbon atoms) with a hydrocarbon. Most preferred is a combination of ethanol and hexane. Simple experimentation will determine other solvents suitable for the present process. Temperature is not critical, but salts are generally best formed at elevated temperatures, e.g., 40°–100° C., conveniently between 40° C. and the reflux temperature of the solvent. It is not essential that complete solution occur at any stage, i.e., the salt can crystallize prior to complete solution of the starting racemic acid (III). The crystalline resolved salt is usually recovered after

SCHEME I

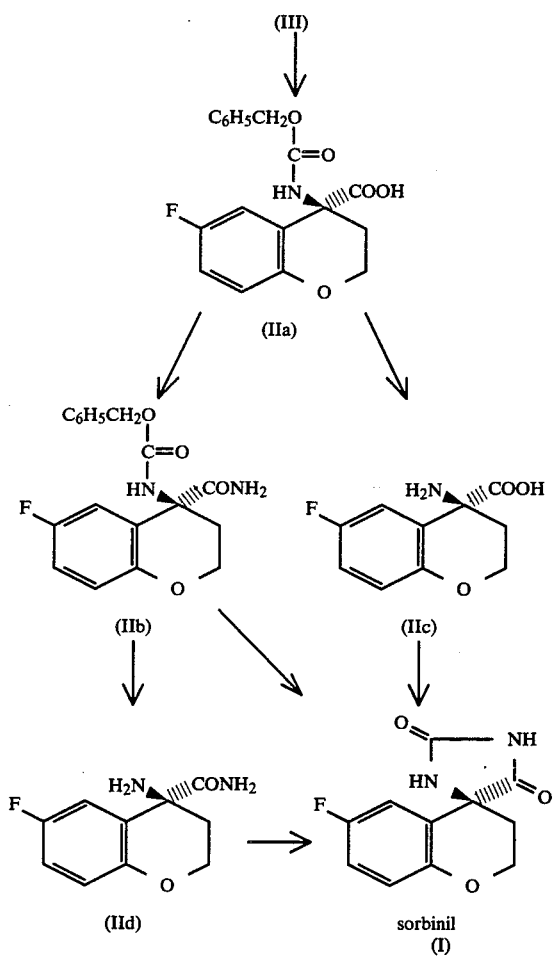

lowering the temperature, e.g., to 0°–40° C., and, if desired, digesting the product by stirring for 1 to 24 hours at the temperature used for isolation. If further purification of the resolved salt is desired, the initially recovered salt can be repulped or recrystallized from the same or another solvent, as delineated above.

The resolved salt, if desired, is converted to its acid form (IIa) by standard techniques of acidification and extraction. If further desired, the free acid is converted to an alternative cationic salt form, such as the sodium, potassium, calcium or ammonium salt, according to methods which are standard in the chemical art. Furthermore, the resolving agent, if desired, is recovered from aqueous raffinates by standard techniques of basification and extraction.

The required racemic benzyloxycarbonylaminocarboxylic acid (III) is prepared by N-benzyloxycarbonylation of 6-fluoro-4-aminochroman-4-carboxylic acid. The preferred preparation of the required aminoacid is by hydrolysis of the racemic hydantoin (A) according to the prior method of our U.S. Pat. No. 4,435,578. The hydantoin (A) is in turn readily prepared from 6-fluoro-4-chromanone in one step according to the method of Sarges, U.S. Pat. No. 4,130,714.

Conversion of the hydantoin (A) to the aminoacid is accomplished under a variety of aqueous, basic conditions. Suitable bases are sodium, potassium and barium hydroxide, used in excess (e.g., 2-4 moles of base/mole of hydantoin) in water at 75°-150° C., conveniently at reflux, but optionally under higher pressure if higher temperatures are desired to ensure complete reaction in a shorter time period. The preferred base is sodium hydroxide, using about 4 moles of base/mole of hydantoin. The aminoacid can be recovered by neutralization or acidification and solvent displacement. Because the aminoacid is usually prepared in water, an alternative method is to N-benzyloxycarbonylate the amino acid in situ, i.e., without isolation. Thus the aqueous reaction mixture containing aminoacid is simply treated with benzyloxycarbonyl chloride, usually in excess, while maintaining basic conditions (e.g., pH 8-9) by simultaneous addition of a base (e.g., 4N NaOH).

In one alternative for further deriving sorbinil, the resolved free acid (IIa), or a cationic salt thereof (not excluding the 1-(−)-alpha-methylbenzylamine salt), is converted to S-6-fluoro-4-(benzyloxycarbonylamino)-chroman-4-carboxamide (IIb). This transformation is carried out by methods which are standard in the chemical art, according to which an activated form of the acid (acid chloride, mixed anhydride) is reacted with ammonia; or the acid is coupled directly with ammonia by use of a dehydrative coupling agent such as N,N'-carbonyldiimidazole. A particularly convenient method is to convert the acid (IIa), in the form of an alkali metal or preferably a tert-amine salt (such as the N-methylmorpholine salt) which is most simply formed in situ from the free acid, with at least one equivalent of a ($C_1$-$C_5$) alkyl, benzyl or phenyl chloroformate (such as isobutyl chloroformate) in a reaction-inert solvent (such as toluene, methylene chloride or tetrahydrofuran). It is preferred to form the mixed anhydride at reduced temperature (10° C. to −15° C.). Once formed in situ, the mixed anhydride is reacted with ammonia, conveniently in excess, introduced as a gas or as a solution in the same or another reaction-inert solvent. Again, it is preferred to react the ammonia with the mixed anhydride at the same reduced range of temperature. Once reaction is complete, the product is recovered by standard methods, usually at ambient temperature.

The chiral benzyloxycarbonylamino carboxamide (IIb) is readily converted to sorbinil (I) by warming in a reaction-inert solvent with a base of sufficient strength to form the carboxamide anion and in an amount at least sufficient to neutralize the resulting sorbinil in the reaction mixture. Suitable bases are alkali metal ($C_1$-$C_5$) alkoxides such as sodium methoxide or potassium tert-butoxide; ($C_1$-$C_5$)alkanols (such as methanol) are particularly suitable as solvent; temperature is not critical, but is suitably in the range of 50°-100° C., conveniently at the reflux temperature of a solvent which boils in this range.

Alternatively, chiral benzyloxycarbonylaminocarboxamide (IIb) is hydrogenolyzed over a hydrogenation catalyst in a reaction-inert solvent to produce S-6-fluoro-4-aminochroman-4-carboxamide (IId). Raney nickel or one of the noble metals, in supported or unsupported form, is well-suited as catalyst. A preferred catalyst is palladium supported on carbon. Suitable solvents include ($C_1$-$C_5$)alkanols, such as methanol. Temperature and pressure are not critical—conveniently ambient temperatures and low pressure (1-10 atmospheres) are employed. If desired, the aminocarboxamide (IId) may be isolated as the free amine, or converted to an acid addition salt, such as the hydrochloride, nitrate, hydrogen sulfate or succinate, by standard methods.

The chiral aminocarboxamide (IId) is readily converted to sorbinil by reaction with a compound of the formula

wherein X and Y are both 1-imidazolyl or X and Y are each independently chloro, trichloromethoxy, ($C_1$-$C_5$)-alkoxy, phenoxy or benzyloxy in a reaction-inert solvent in the presence of a base which is of sufficient strength to form the anion of the carboxamide (as defined above) in an amount which is sufficient to neutralize the sorbinil, any HCl produced in the reaction, and the acid of any acid addition salt which may have been employed in the reaction. Conditions particularly well-suited for this reaction are to employ a ($C_1$-$C_5$) dialkyl carbonate (such as dimethyl carbonate) in a ($C_1$-$C_5$) alkanol (such as methanol), with an alkali metal ($C_1$-$C_5$) alkoxide (such as sodium methoxide or potassium tert-butoxide) as base. When phosgene or a chloroformate is used under these conditions, it will be noted that the reagents will be converted, at least in part, to the methyl carbonate prior to formation of the sorbinil. It will be evident that when the reagent is a dicarbonate or a chloroformate (used per se or formed in situ from phosgene or chloroformate and alkoxide or an alcohol used as solvent), the reaction will occur at least in part via a 4-acyloxyamino-4-carboxamide compound [such as the above compound of the formula (IIb), when benzyl chloroformate is employed as reagent]. Temperature is not critical, although temperatures in the range of 50°-100° C. are usually preferred.

In yet another alternative, the resolved benzyloxycarbonylamino acid (IIa) is hydrogenolyzed to chiral S-6-fluoro-4-aminochromane-4-carboxylic acid (IIc) by hydrogenolysis employing conditions as described above for the hydrogenolysis of S-6-fluoro-4-(benzyloxycarbonylamino)chroman-4-carboxamide. The product is isolated as the aminoacid per se, or, if preferred, converted to an acid addition or cationic salt by methods which are standard in the chemical art, as noted above.

The aminoacid (IIc) is readily converted to sorbinil (I) by reaction with at least one molar equivalent of an alkali metal cyanate (e.g., NaOCN) in a reaction inert solvent in the presence of at least one molar equivalent of an acid. The preferred conditions employ acetic acid as both solvent and acid. Temperature is not critical and is usually in the range of ambient (about 20° C.) to 100° C. To force the reaction to completion within a reasonable time, temperatures higher in this range are generally employed toward the end of the reaction period.

As used hereabove, the expression "reaction-inert solvent" refers to a solvent which does not interact with starting materials, reagents, intermediates or products in a manner which has a significant adverse effect on the yield of the desired product.

The efficiency of the overall process from 6-fluoro-4-chromanone to sorbinil is greatly increased by recovering crude enantiomer of the sorbinil precursor (IIa) from mother liquors, preferably also recovering the amine resolving agent, using standard techniques of basification/acidification and extraction. The enantiomeric material is recycled to 6-fluoro-4-chromanone by the hydrolysis/oxidation method of Cue, Massett and Hammen, U.S. Pat. No. 4,431,828.

The present invention is illustrated by the following examples. However, it should be understood that the invention is not limited to the specific details of these examples. All temperatures are ambient unless otherwise specified.

PREPARATION 1

RS-4-Amino-6-fluorochroman-4-carboxylic Acid

Method A

A stirred slurry of RS-6-fluorospiro[chroman-4,4'-imidazolidine]-2',5'-dione, (78 g, 0.33 mol) and Ba(OH)$_2$. 8H$_2$O (208.3 g, 0.66 mol) in 585 ml H$_2$O was slowly heated to reflux over 3 hours and refluxed 16 hours. The slurry was cooled to 80° and powdered (NH$_4$)$_2$CO$_3$ (78 g) added portionwise over 5 minutes. Moderate foaming was noted. After stirring 1.5 hours at 80°, the mixture was cooled to 60° and filtered over diatomaceous earth with 2×100 ml hot H$_2$O for wash. The combined filtrate and washes were stripped to 200 ml and allowed to stand overnight. 2-Propanol (600 ml) was added and the mixture heated to 70° to dissolve precipitated solids. The hot solution was treated with activated carbon, filtered over diatomaceous earth and washed with hot 1:1 H$_2$O:2-propanol. The combined filtrate and washes were stripped to 200 ml, and water chased with 3×300 ml fresh 2-propanol. The resulting thick slurry was diluted with 200 ml additional 2-propanol, cooled to 5°, granulated 0.5 hour, filtered and air dried to yield title product, 63.6 g, 91.2%, m.p. 252°-253° C. (dec.).

Method B

RS-6-fluorospiro[chroman-4,4'-imidazolidine]-2',5'-dione (236.2 g, 1.0 mol) was slurried in 2300 ml H$_2$O. NaOH pellets (160.0 g, 4.0 mol) were added to yield a warm solution (50° C.) which was heated at 95° C. for 48 hours, cooled to room temperature and the pH lowered from 12.3 to 5.2 with 340 ml 12N HCl. The resulting slurry was filtered and the filtrate evaporated in vacuo to solids (397 g), which were stirred with 5 liters methanol, filtered and the filtrate evaporated to 600 ml of a slurry. The slurry was diluted with 500 ml ethyl acetate and solid title product, contaminated with salt, recovered by filtration (147 g). Evaporation of the mother liquor, chased 2×500 ml ethyl acetate gave additional salt contaminated product (74 g).

PREPARATION 2

RS-6-Fluoro-4-(benzyloxycarbonylamino)chroman-4-carboxylic Acid

Method A

Title product of the preceding Preparation (Method A, 7.9 g, 0.037 mol) was stirred in 200 ml of pyridine. To the resulting hazy solution was added benzyloxycarbonyl chloride (7.5 g, 6.28 ml, 0.044 mol). The resulting clear solution was stirred for 18 hours at ambient temperature, then concentrated in vacuo to a light yellow oil. The oil was dissolved in 300 ml CHCl$_3$, extracted 3×300 ml 10% HCl, and the combined aqueous acid layers extracted 1×150 ml CHCl$_3$. The CHCl$_3$ layers were combined, washed 1×200 ml saturated NaCl, dried (MgSO$_4$) and evaporated in vacuo to white solids (8.1 g) which were repulped in hexane to yield purified title product as a mostly amorphous solid, 7.77 g, m.p. 145°-153° C.

Method B

The same starting imidazolidine used in the preceding Preparation (47.2 g, 0.2 mol) and NaOH pellets (28 g, 0.7 mol) were combined in 400 ml H$_2$O and heated to 98° C. for 24 hours. The reaction mixture was cooled to 23° C. and the pH was lowered from 11.8 to 5.5 with concentrated HCl. Unhydrolyzed starting material (14.0 g) was recovered by filtration. The filtrate was diluted with 100 ml acetone and the pH adjusted to 8.3 with 4N NaOH. Benzyloxycarbonyl chloride (34 g, 0.2 mol) was added dropwise over 1 hour, maintaining the pH at 8.3–8.5 with 4N NaOH. After stirring 18 hours, the reaction mixture was extracted 2×100 ml CH$_2$Cl$_2$, acidified to pH 2.0 with 12N HCl and extracted 2×300 ml fresh CHCl$_3$. The acid CHCl$_3$ extracts were combined, washed with H$_2$O, dried and concentrated to 50 ml in vacuo. The resulting slurry was diluted with 100 ml hexane and title product recovered by filtration as an amorphous solid, 5.0 g, m.p. 130°-150° C.; tlc Rf 0.7 (142:30:7 ethyl acetate:methanol:acetic acid)—homogeneous and identical with product of Method A.

Method C

Salt contaminated title product of the preceding Preparation (Method B, both crops, 219 g) was added over 5 minutes to thionyl chloride (143 ml, 233 g, 1.96 mols) in 1000 ml methanol at 0° C. The mixture was stirred 30 minutes at room temperature, then at 65° C. for 30 minutes and finally for 18 hours at room temperature. The mixture was cooled to 10° C. and fresh SOCl$_2$ (50 ml, 0.69 mol) added over 30 minutes, then refluxed for 3 hours, and again cooled to 10° C. More SOCl$_2$ (50 ml, 0.69 mol) was added over 1 hour and the mixture finally refluxed 18 hours, cooled to room temperature and clarified by filtration. The filtrate was evaporated in vacuo to tacky solids, taken up in 1000 ml cold H$_2$O and 500 ml ethyl acetate. The aqueous layer was separated, extracted 3×100 ml fresh ethyl acetate, layered with 500 ml CH$_2$Cl$_2$ and the pH adjusted to 10 with 4N NaOH. The aqueous layer was separated and extracted 3×100 ml CH$_2$Cl$_2$. The CH$_2$Cl$_2$ layers were combined, washed 1×400 ml H$_2$O and then 1×200 ml saturated NaCl, dried over MgSO$_4$ and evaporated in vacuo to yield methyl RS-4-amino-6-fluorochroman-4-carboxylate, 124.4 g, m.p. 63°-66° C.

A portion of that intermediate methyl ester (11.25 g, 0.05 mol) was dissolved by stirring in 100 ml pyridine for 5 minutes and cooled to 5°–10° C. Benzyloxycarbonyl chloride (17 g, 0.1 mol) was added dropwise over 15 minutes maintaining temperature at or below 20° C. The mixture was stirred 18 hours at room temperature, clarified by filtration, and then concentrated in vacuo to an oily residue (29 g). The latter was taken up in 150 ml CHCl$_3$; washed in sequence 1×100 ml H$_2$O, 2×100 ml 0.5N HCl and 1×200 ml saturated NaHCO$_3$; dried over MgSO$_4$, and concentrated to a second oil (18.7 g), which was dissolved in 150 ml CH$_3$OH and added to 50 ml H$_2$O containing NaOH (6 g, 0.15 mol). The resulting two phase system was stirred at 35° C. to achieve solution and hydrolysis of the methyl ester, then evaporated to 50 ml, diluted with 150 ml H$_2$O, extracted 2×50 ml CHCl$_3$, and layered with 200 ml CH$_2$Cl$_2$. The pH was adjusted from 12 to 1.8 with 30 ml 6N HCl. The organic layer was separated, washed 1×100 ml H$_2$O, dried over MgSO$_4$ and evaporated to 100 ml of a crystalline slurry. Hexane (100 ml) was twice added and reevaporated to 100 ml. Crystalline title product was recovered by filtration, 13.6 g; 79%; m.p. 160°–162° C.

EXAMPLE 1

1-(−)-alpha-Methylbenzylammonium S-6-Fluoro-4-(benzyloxycarbonylamino)chroman-4-carboxylate Racemic 6-fluoro-4-(benzyloxycarbonylamino)chroman-4-carboxylic acid (690 mg, 0.002 mol) was dissolved in 4 ml of absolute ethanol. To the resulting hazy solution was added 1-(−)-alpha-methylbenzylamine (242 mg, 0.002 mol) in 3 ml absolute ethanol. The resulting clear solution was stirred briefly and then diluted with 15 ml of hexane over a 5 minute period. Crystallization began within 5 minutes. After stirring for one hour, crude product was recovered by filtration, 730 mg [alpha]$_D^{20}$+6.0° (c=0.5 in methanol). A portion of the crude product (680 mg) was dissolved in 7 ml of absolute ethanol at 50° C. Hexane (7 ml) was added and the solution cooled with stirring to room temperature. Purified, crystalline title product was recovered by filtration, 310 mg, [alpha]$_D^{20}$+53.4 (c=0.5 in methanol).

Alternatively, title product was obtained without need for recrystallization by dissolving racemic 6-fluoro-4-(benzyloxycarbonylamino)chroman-4-carboxylic acid (345 mg, 0.001 mol) in 4 ml of absolute ethanol. 1-(−)-alpha-Methylbenzylamine (125 mg, 0.001 mol) in 4 ml of absolute ethanol was added. After brief stirring, 15 ml of hexane was added. After several minutes title product began to crystallize and was recovered after 30 minutes of granulation, 190 mg, m.p. 163°–165° C., [alpha]$_D^{20}$+51° (c=0.5 in methanol).

On a larger scale, racemic 6-fluoro-4-(benzyloxycarbonylamino)chroman-4-carboxylic acid (44 g, 0.127 mol) in 600 ml of absolute ethanol was stirred at 22°–23° C. as 1-(−)-alpha-methylbenzylamine (15.4 g, 0.127 mol) in 40 ml of absolute alcohol was added. After stirring 5 minutes, hexane (640 ml) was added portionwise over 10 minutes. The resulting mixture was stirred for 2 hours, during which title product crystallized and product was recovered by filtration, 24 g; [alpha]$_D^{20}$+51.5 (c=1 in methanol); m.p. 163°–166° C. The entire batch was dissolved in 220 ml absolute ethanol at 70° C. and stirred as 440 ml hexane was added over 5 minutes. The resulting solution began to crystallize at 55° C. It was cooled to 23° C., digested for one hour, and title product recovered by filtration, 21.6 g; 73%; [alpha]$_D^{20}$53.7 (c=1 in methanol).

EXAMPLE 2

S-6-Fluoro-4-(benzyloxycarbonylamino)-chroman-4-carboxylic Acid

Title product of the preceding Example (260 mg) was slurried in 20 ml of H$_2$O and the pH lowered to 1.0 with 3N HCl. The system was layered with 30 ml CHCl$_3$. The aqueous layer was separated and extracted 2×20 ml fresh CHCl$_3$. The organic layers were combined, dried over MgSO$_4$ and stripped in vacuo to a gum. The latter was triturated with 10 ml of toluene and after stirring for 1 hour filtered to yield solid title product, 150 mg; [alpha]$_D^{20}$+60.2° (c=0.5 in methanol).

On a larger scale, title product of the preceding Example (21 g) was stirred at 23° C. with 200 ml H$_2$O and 200 ml CHCl$_3$ as the pH was lowered from 6.5 to 1.5 with concentrated HCl. After stirring for 5 minutes at a stable pH of 1.5 the layers were separated and the aqueous layer extracted with 2×50 ml fresh CHCl$_3$. The three organic layers were combined, washed 2×100 ml H$_2$O, dried (MgSO$_4$) and concentrated to an oil which was crystallized by stirring with 100 ml toluene for 10 minutes. The resulting slurry was diluted with 100 ml hexane, granulated 30 minutes and title product recovered by filtration, 14.7 g; [alpha]$_D^{20}$+60.8 (c =0.69 in methanol); tlc Rf 0.8 (75:75:2 ethyl acetate:hexane:acetic acid).

EXAMPLE 3

S-6-Fluoro-4-(benzyloxycarbonylamino)-chroman-4-carboxamide

Title product of the preceding Example (89 g, 0.258 mol) was slurried in 860 ml toluene. N-methylmorpholine (28.4 g, 0.28 mol) was added producing a solution after stirring for 5 minutes. The solution was cooled to −9° C. and isobutylchloroformate (37.9 g, 0.277 mol) added portionwise over 30 minutes, maintaining a temperature of −5° to −10° C. After stirring the reaction mixture for a further 45 minutes at −10° C., gaseous NH$_3$ was added over the stirred surface for 30 minutes, then under the surface for 20 minutes, maintaining a temperature of −2° to −9° C. by the rate of addition. The reaction mixture was then stirred at −5° to −10° C. for 1 hour, then warmed to ambient temperature, and diluted with 500 ml H$_2$O. The aqueous layer was separated, washed 1×100 ml toluene, and the organic layers combined, washed in sequence with 2×250 ml H$_2$O, dried over MgSO$_4$ and stripped to yield title product as a tacky oil, 81 g; [alpha]$_D^{20}$+41.25 (c=1 methanol); homogeneous by tlc Rf 0.7 (75:75:2 ethyl acetate:hexane:acetic acid).

EXAMPLE 4

S-6-Fluoro-4-aminochroman-4-carboxamide

Title product of the preceding Example (80 g) in 150 ml methanol was combined with 1 g 5% Pd/C (50% wet) and hydrogenated under 3–4 atmospheres of hydrogen for 2.5 hours by which time uptake of hydrogen was complete. Catalyst was recovered by filtration with 30 ml of methanol wash. The combined filtrate and wash were stripped in vacuo to yield 52 g of title product as an oil. The oil was taken up in 40 ml of isopropanol, warmed to 65° C. and slowly added to 80 ml of hexane, maintaining a temperature of 58° C., during which the product crystallized. Additional hexane (160 ml) was added over 10 minutes, the slurry cooled to room temperature, and filtered to yield crystalline title product, 29.6 g; m.p. 105°–106° C.; $[alpha]_D^{20} + 10.0°$ (c=1, methanol). The filtrate was stripped in vacuo to yield additional product as an oil, 14.7 g, which crystallized on standing.

EXAMPLE 5

S-6-Fluoro-4-aminochroman-4-carboxylic Acid

Title product of Example 2 (6.9 g) in 100 ml of methanol was combined with 0.5 g of 5% Pd/C (50% wet) and hydrogenated at 3–4 atmospheres for 2 hours (uptake of hydrogen was complete after 0.5 hours). Catalyst was recovered by filtration, and the filtrate concentrated to damp solids which were triturated with toluene. Title product was recovered by filtration, 3.9 g; m.p. 255° C. (dec.); $[alpha]_D^{20} + 85.6$ (c=0.52 in methanol); tlc Rf 0.2 (142:30:7 ethyl acetate:methanol:acetic acid), positive to ninhydrin spray.

EXAMPLE 6

Sorbinil

Method A

S-6-Fluoro-4-aminochroman-4-carboxamide (2.1 g, 0.01 mol), dimethylcarbonate (1.8 g, 0.02 mol) and sodium methoxide (0.54 g, 0.01 mol) were combined in 25 ml dry methanol, and, after stirring for 30 minutes, heated to reflux for 2.5 hours. The reaction mixture was cooled to 30° C., charged with fresh dimethylcarbonate (0.90 g, 0.01 mol) and sodium methoxide (0.54 g, 0.01 mol), and refluxed for an additional 1.5 hours. The reaction mixture was recooled, stripped in vacuo, the residue taken up in 100 ml H₂O and extracted 2×50 ml CHCl₃. The aqueous phase was stripped slightly to remove traces of CHCl₃ and then stirred as pH was lowered to 2.0 with 3N HCl. The resulting crystalline slurry was granulated for one hour and filtered to yield title product, 1.93 g; m.p. 237°–240° C.; $[alpha]_D^{20} + 55.2$ (c=0.5, methanol).

Alternatively, S-6-fluoro-4-aminochroman-4-carboxamide (210 mg, 0.001 mol) and dimethylcarbonate (7 ml) were combined in 7 ml methanol with stirring. Potassium tert-butoxide (112 mg, 0.001 mol) was added and the mixture refluxed for 60 hours. The reaction mixture was stripped in vacuo, the residue taken up in 15 ml H₂O, and the pH adjusted to 2.0 with 3N HCl. Crude title product was recovered by filtration, 147 mg; m.p. 180°–210° C. The latter was stirred in 0.5 ml ethyl acetate and filtered to yield purified title product, 61 mg.

Method B

S-6-Fluoro-4-(benzyloxycarbonylaimino)chroman-4-carboxamide (345 mg, 0.001 mol) and sodium methoxide (54 mg, 0.001 mol) were combined in 15 ml methanol. After stirring for 15 minutes, the mixture was heated to reflux for 1.5 hours, then cooled and concentrated in vacuo to a sticky oil. The oil was dissolved in 15 ml H₂O and acidified to pH 1.0 with 3 ml of 3N HCl. The slurry was granulated for 15 minutes and title product recovered by filtration, 155 mg; m.p. 238°–241° C.; $[alpha]_D^{20} + 55°$ (c=0.4 in methanol).

Method C

S-6-Fluoro-4-aminochroman-4-carboxylic acid (2.1 g, 0.01 mol) in 30 ml acetic acid was stirred as 1.3 g (0.02 ml) of sodium cyanate was added in portions over 10 minutes. After stirring 18 hours at ambient temperature, another portion of sodium cyanate (1.3 g, 0.02 mol) was added. The mixture was stirred 2 hours at room temperature and then for 2 hours at 95° C. The reaction mixture was cooled, concentrated to dryness in vacuo, the residue taken up in 50 ml of water and extracted 3×50 ml ethyl acetate. The organic layers were combined, washed 2×50 ml H₂O, dried (MgSO₄) and evaporated in vacuo to a semisolid (4 g). The latter was triturated with 20 ml isopropanol, the slurry diluted with 20 ml hexane and title product recovered by filtration, 800 mg; m.p. 239°–242° C.; $[alpha]_D^{20} + 55.1°$ (c=1 in methanol).

We claim:

1. A chiral compound of the formula

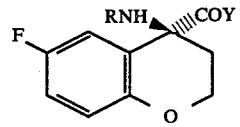

wherein R is hydrogen or benzyloxycarbonyl and Y is hydroxy or amino, a cationic salt thereof when Y is hydroxy or an acid addition salt thereof when R is hydrogen.

2. The compound of claim 1 wherein R is benzyloxycarbonyl and Y is hydroxy, or a cationic salt thereof.

3. The compound of claim 2 in the form of its cationic salt with 1-(−)-alpha-methylbenzylamine.

4. The compound of claim 1 wherein R is hydrogen and Y is hydroxy, or a cationic or acid addition salt thereof.

5. The compound of claim 1 wherein R is benzyloxycarbonyl and Y is amino.

6. The compound of claim 1 wherein R is hydrogen and Y is amino, or an acid addition salt thereof.

* * * * *